US00PP28088P3

(12) United States Plant Patent
Delbard

(10) Patent No.: US PP28,088 P3
(45) Date of Patent: Jun. 6, 2017

(54) ***DAHLIA* PLANT NAMED 'PEACH FLAMINGO'**

(50) Latin Name: *Dahlia variabilis*
Varietal Denomination: Peach Flamingo

(71) Applicant: Arnaud Delbard, Malicorne (FR)

(72) Inventor: Arnaud Delbard, Malicorne (FR)

( * ) Notice: Subject to any disclaimer, the term of this patent is extended or adjusted under 35 U.S.C. 154(b) by 68 days.

(21) Appl. No.: 14/545,836

(22) Filed: Jun. 26, 2015

(65) Prior Publication Data

US 2016/0381855 P1 Dec. 29, 2016

(51) Int. Cl.
*A01H 5/02* (2006.01)

(52) U.S. Cl.
USPC ..... Plt./321

(58) Field of Classification Search
USPC ..... Plt./321
See application file for complete search history.

(56) References Cited

PUBLICATIONS

Spirgen Greenhouse Management Jul. 2014 digital flipbook, retrieved on Oct. 27, 2016, retrieved from the Internet at <http://www.greenhousemag.com/fileuploads/digital-editions/gm/digital/201407/html5/index.html?page=105> 6 pp.*

* cited by examiner

*Primary Examiner* — June Hwu
(74) *Attorney, Agent, or Firm* — Barbara Campbell; Bethany R. Roahrig; Cochran Freund & Young, LLC

(57) ABSTRACT

A new cultivar of *Dahlia* plant named 'Peach Flamingo' that is distinguishable by its naturally branched plant habit with multiple basal branches and lateral branches, markedly dentate compound leaves, and large peach-colored cactus type flowers, is disclosed.

2 Drawing Sheets

Genus and species: *Dahlia variabilis.*
Variety denomination: 'Peach Flamingo'.

BACKGROUND OF THE NEW PLANT

The present invention relates to a new and distinct cultivar of *dahlia* grown for use in mixed combinations, beds and the landscape. The new variety is known botanically as *Dahlia variabilis* and will be referred to hereinafter by the cultivar name 'Peach Flamingo'.

The genus *Dahlia* is in the family Compositae . The flower of 'Peach Flamingo' is classified as a Cactus-type inflorescence whose ray flowers (appearing as petals) are rolled for approximately half of their length and are flat at the base. The ray flowers are arranged in whorls surrounding a central cluster of disc florets.

The inventor's *Dahlia* breeding program was commenced in 2007 in Commentry in central France. The objective of the breeding program is to combine certain desirable commercial characteristics including large cactus-type flowers with many petals, decorative foliage, novel colors and color combinations and a naturally dwarf and branching habit which eliminates the necessity to apply chemical growth regulators or repeated manual pinching.

The inventor's breeding stock consists of an isolated plot of *dahlia* varieties (named and unnamed) which have been selected or raised by the inventor from previous generations. The inventor allows open pollination of the breeding stock, but positions possible parents in particular proximities in order to increase the opportunity for desirable crosses. The potential parent varieties are planted in May of each year and seed is harvested and stored in October and November of the same year. Seeds are sown in March of the following year, planted into the open ground in June and evaluated and, if very promising, set aside in August. Those selections which the inventor considers worthy of introduction are multiplied in the fall of the year of selection in the inventor's tissue culture laboratory. Typically, from sowing 2,500 harvested seeds, approximately 5 seedlings will be put forward for commercial performance trials and potential introduction.

'Peach Flamingo' arose from the breeding program described above and was selected by the inventor in August 2012. The inventor selected 'Peach Flamingo' for its large peach-colored cactus-type flowers which are borne on sturdy and naturally branching plants.

The parents of 'Peach Flamingo' are unknown seedlings or varieties of cactus-type *dahlias.*

The first asexual reproduction of 'Peach Flamingo' was conducted in fall 2012 using micro cuttings in the inventor's laboratory in Commentry, France. Subsequent asexual propagation was carried out by stem cuttings at the inventor's nursery starting in April 2013. Since that time under careful observation, the distinguishing characteristics have been determined stable, uniform, and to be reproduced true to type in subsequent generations of asexual propagation.

SUMMARY

The following traits have been repeatedly observed and represent the distinguishing characteristics of the new *Dahlia* cultivar named 'Peach Flamingo'. These traits in combination distinguish 'Peach Flamingo' from all other existing varieties of *Dahlia* known to the inventor. 'Peach Flamingo' has not been tested under all possible conditions and phenotypic differences may be observed with variations in environmental, climatic, and cultural conditions, however, without any variance in genotype.

1. 'Peach Flamingo' exhibits naturally branched plant habit with multiple basal branches and lateral branches.
2. 'Peach Flamingo' bears markedly dentate compound leaves.
3. 'Peach Flamingo' bears large cactus-type flowers which are peach in color.
4. 'Peach Flamingo' is grown for use in mixed combinations, beds and the landscape.
5. 'Peach Flamingo' blooms from summer until fall.
6. 'Peach Flamingo' grows to 40 cm to 50 cm in height and 40 cm to 50 cm in width after one growing season.
7. 'Peach Flamingo' is hardy to USDA Zone 9.

DESCRIPTION OF THE PHOTOGRAPHS

The accompanying color photographs labeled FIG. 1 and FIG. 2 illustrate the overall appearance of the new *Dahlia* cultivar named 'Peach Flamingo' showing the colors as true as is reasonably possible to obtain in colored reproductions of this type. Colors in the photographs may differ from the color values cited in the detailed botanical description, which accurately describes the actual colors of the new *Dahlia* variety named 'Peach Flamingo'. The photographs were made from digital photographs of plants grown outdoors in Commentry, France.

DESCRIPTION OF THE NEW VARIETY

Figure 1:
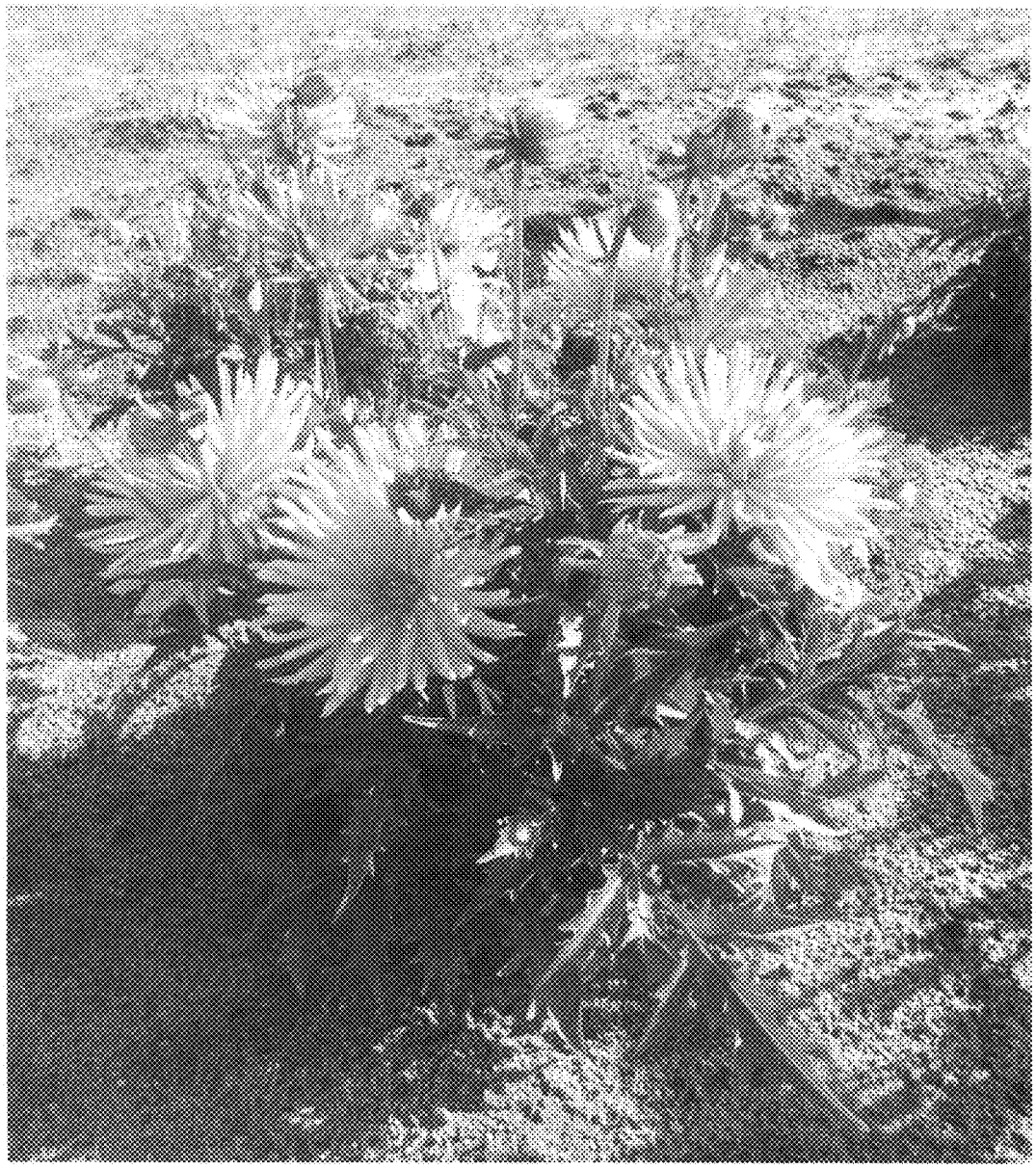
FIG. 1 depicts the entire plant in bloom showing the overall appearance of 'Peach Flamingo' with typical bloom, foliage and habit grown in an outdoor nursery.
Figure 2:
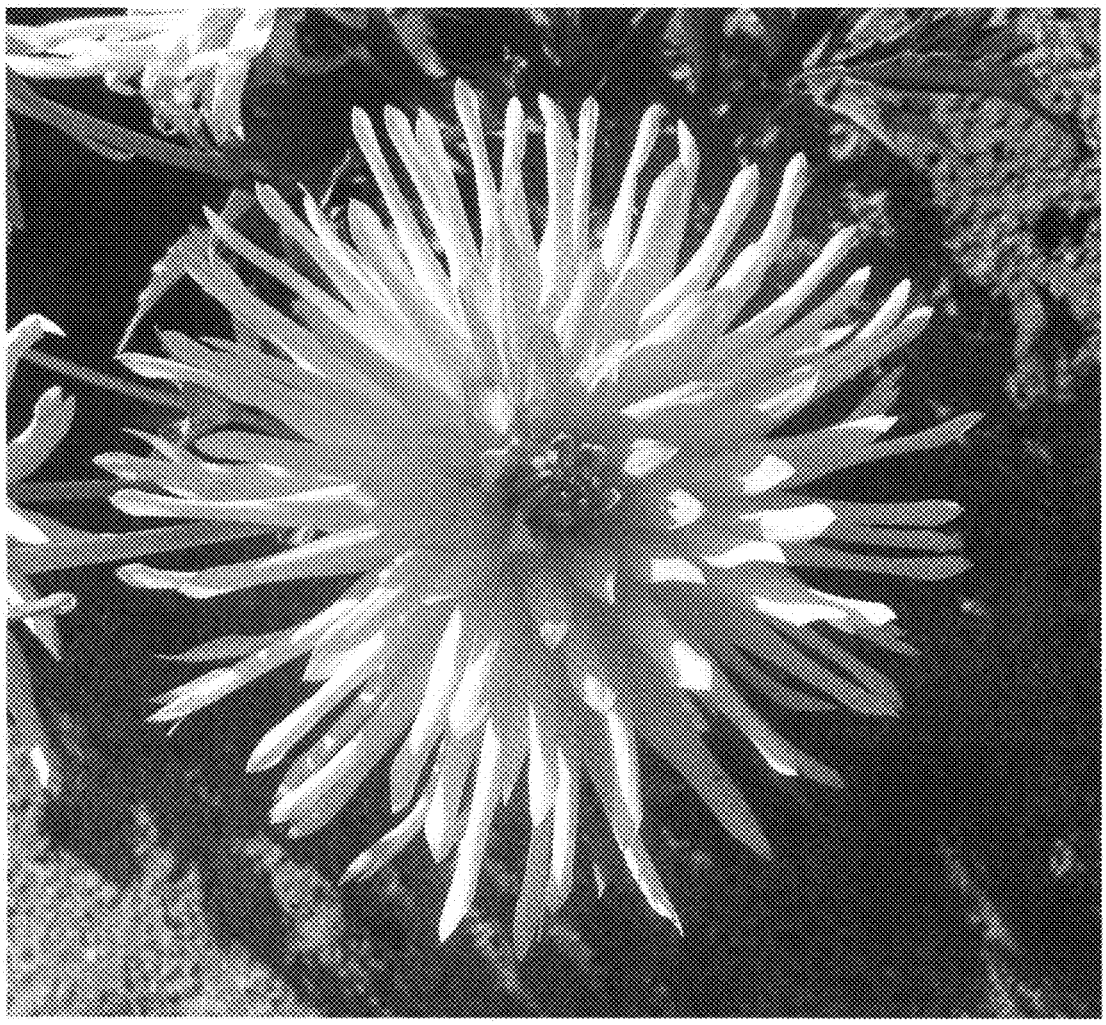
FIG. 2 depicts a close-up view of a flower of 'Peach Flamingo'

The following is a detailed botanical description of the new *Dahlia* cultivar named 'Peach Flamingo'. Observations, measurements, values and comparisons were collected during April and May 2015 in Santa Barbara, Calif. from 2-liter container plants. Color determinations were made in accordance with The 2007 Royal Horticultural Society Colour Chart from London England, except where general color terms of ordinary dictionary significance are used. Growing requirements are similar to the species.

Botanical classification:

*Family*.—Compositae.

*Genus and species*.—*Dahlia variabilis*.

*Denomination*.—'Peach Flamingo'.

*Common name*.—*Dahlia*.

Parentage: 'Peach Flamingo' is a seedling selection made from plants grown from seed which resulted from the open-pollination of unknown and unnamed parent seedlings retained from previous generations in the breeding program.

Plant:

*Propagation method*.—Tissue culture, cuttings, tubers.

*Rooting system*.—Fine and fibrous.

*Tuber shape*.—Fusiform.

*Tuber size*.—10 cm average.

*Tuber color*.—165D.

*Vigor*.—Vigorous.

*Habit*.—Upright habit.

*Use*.—For use in mixed combinations, beds and the landscape.

*Type*.—Perennial in climate zones 9 and above; annual elsewhere.

*Dimensions*.—40 cm to 50 cm in height and 40 cm to 50 cm in width.

*Cultural requirements*.—Grow in full sun with regular water, and well-draining potting soil.

*Pest susceptibility*.—Susceptible to aphids.

*Disease susceptibility*.—Susceptible to mildew in highly humid conditions.

*Hardiness*.—USDA Zone 9.

Stem and basal branches:

*Basal branching habit*.—Naturally occurring (unpinched) basal branches with lateral branches.

*Basal branches*.—Number: 3 to 5. Dimensions: 45 cm in length and 0.4 cm in width. Shape: Cylindrical. Surface: Glabrous. Internode length (average): 7 cm.

*Lateral branches*.—Dimensions: 45 cm in length and 0.4 cm in width. Shape: Cylindrical. Surface: Glabrous.

*Internode length* (*average*).—7 cm.

Foliage:

*Type*.—Compound.

*Division*.—Bi-pinnately compound consisting of two pairs of tri-lobed lateral leaflets and one tri-lobed terminal leaflet.

*Compound leaf dimensions*.—24 cm to 30 cm in length and 24 cm to 28 cm in width.

*Leaf wing*.—Not present (or not observed).

*Leaflet dimensions*.—First pair (nearest stem) of lateral leaflets: Length 13 cm, width 6 cm. Second pair of lateral leaflets: Length 10 cm, width 5.5 cm. Terminal leaflet: Length 10 cm to 11 cm, width 7 cm to 8 cm.

*Leaflet attachment*.—First pair (nearest stem) of lateral leaflets: Petiolule. Second pair of lateral leaflets: Sessile to rachis. Terminal leaflet: Petiolate to rachis.

*Leaflet shape, base, apex, margin, color, venation, surface are all identical for lateral leaflets and terminal leaflets as follows*.—Base: Attenuate. Apex: Apiculate. Margin: Coarsely and irregularly dentate with tiny short fine silver-gray hairs, approximately 0.25 mm in length; teeth length 0.5 cm to 1.5 cm, width 0.4 cm to 0.8 cm; approximately 6 teeth per margin (12 teeth per leaflet). Color (adaxial surface): 137B. Color (abaxial surface): 138C. Venation pattern: Pinnate. Vein color (adaxial surfaces): 138B. Vein color (abaxial surface): 137C. Leaf surfaces (both surfaces): Glabrous. Leaf attachment: Petiolate. Petiole shape: Sulcate. Petiole dimensions: 6 cm in length and 6mm in width at stem. Petiole color: Adaxial surface is 152A, abaxial surface is 138C. Petiole surfaces: Glabrous.

*Compound leaf rachis* (*from first pair of leaflets to base of terminal leaflet*).—Shape: Sulcate with central midrib. Dimensions: 9 cm in length, 4mm in width at first pair of leaflets. Color: Adaxial surface is 152A, abaxial surface is 138C. Surfaces: Glabrous.

*First pair of leaflet petiolules*.—Shape: Sulcate. Dimensions: 0.5 cm to 1 cm in length, 3 mm in width. Color: Adaxial surface is 152A, abaxial surface is 138C. Surfaces: Glabrous.

Inflorescence:

*Inflorescence type and shape*.—Cactus-type globose inflorescence whose ray flowers (appearing as petals) are rolled for approximately half of their length and are flat at the base; inflorescence is borne above the foliage on near-vertical stems.

*Arrangement*.—The ray flowers are arranged in whorls surrounding a central cluster of disc florets.

*Aspect*.—Facing upward and outward.

*Inflorescence quantity*.—15 to 20 buds and flowers per 2-liter container plant.

*Dimensions of inflorescence*.—10 cm to 15 cm in diameter and 10 cm to 12 cm in height.

*Blooming season*.—Summer and fall.

*Lastingness of inflorescence*.—4 to 5 days.

*Self-cleaning or persistent*.—Self-cleaning.

*Fragrance of inflorescence*.—None observed.

*Peduncle*.—Dimensions (average): 12 cm in length and 0.40 cm in diameter. Shape: Cylindrical. Surface: Glabrous. Strength: Extremely stiff. Color: Ranges between N144A and 151A.

*Bud*.—Shape: Oblate. Dimensions (average): 1.3 cm in height and 1.3 cm in diameter. Surface: Glabrous. Appearance: Semi-glossy. Color: 143B at base becoming N144A with streaks of 42C towards and at apex. Apex: Obtuse. Base: Truncate.

*Ray florets*.—Quantity per inflorescence: 100 to 120. Arrangement: Whorls of 3 to 4 rings. Form: Rolled downwards for approximately half of length; flat at the base; approximately 4 to 6 ray florets appear as sickle-shaped petaloids emerging from perimeter of receptacle. Dimensions (average, including corolla tube): 7 cm in length and 0.8 cm in width. Shape: Lanceolate, rolled (recurved) from apex to approximately midway along length; flat at base. Surface (adaxial and abaxial): Glabrous. Apex: Acute, occasionally notched; depth of notch up to 3 mm. Base: Attenuate. Margin: Entire. Color: A fully open inflorescence with all ray florets fully expanded appears uniformly pale to mid peach in color; when still opening the inner ray florets are orange-red in color giving the appearance of a darker eye to the entire inflorescence. Color (ray florets fully expanded, both surfaces): Ranges between 37C and 37A. Color (inner ray florets opening, still clustered, both surfaces): 33B. Corolla tube, dimensions: 3 mm in length, 1.5 mm in diameter. Corolla tube color: 151D. Ray floret venation: Very faint longitudinal parallel veins, color close to ray floret 37C to 37A.

*Disc florets*.—Disc diameter: 1.5 to 2.0 cm. Quantity of disc florets: Approximately 36 disc florets per inflorescence. Disc floret dimensions: 1.75 cm in length and 0.10 cm in width. Disc floret color: 187A. Petals: 8 in number. Petals fused or unfused: Fused. Petal apex: Acute. Petal surface (ventral and dorsal surfaces): Glabrous. Receptacle dimensions: 1 cm in depth and 1.60 cm in diameter. Receptacle surface: Glabrous. Receptacle color: 187A.

*Phyllaries*.—Arrangement: Whorl, consisting of three concentric rings or layers. Number: Approximately 72 in total; depending on the angle of viewing the inflorescence, some of the phyllaries are behind and under the inflorescence. Shape: Lanceolate. Dimensions: Ranging from 22 mm in length and 9 mm in width (outer ring) to 15 mm in length and 5 mm in width (inner ring). Thickness (middle of base, elsewhere tapers to less than 0.5mm at margin): Ranging from 1.5 mm (outermost phyllaries) to 1.0 mm (innermost phyllaries). Color: (adaxial and abaxial surfaces): Predominantly 1D except narrow elongated triangle 143C at base and extending to midpoint of phyllary. Surface texture: Waxy, glabrous. Appearance: Translucent. Apex: Rounded. Base: Truncate. Margin: Entire.

Reproductive organs:

*Stamens*.—5 in number, fused into tube around style.

*Stamen length*.—5 mm to 6 mm.

*Stamen color*.—166A.

*Anther*.—Connate.

*Anther color*.—23A.

*Pollen*.—Present, large amount.

*Pollen color*.—N163D.

*Pistil*.—One present.

*Pistil length*.—11 mm in length.

*Stigma form*.—Bifid, decurrent.

*Stigma dimensions*.—3 mm in length and 4.50 mm in width (distance between the two apices).

*Stigma color*.—13B.

*Ovary position*.—Inferior.

*Ovary color*.—150D.

*Ovary shape*.—Rotund.

*Ovary dimensions*.—2 mm in width and 3 mm in height.

Seed: No seed observed to date.

COMPARISON TO COMMERCIAL VARIETIES

The varieties of *Dahlia* which are considered to most closely resemble 'Peach Flamingo' are *Dahlia* 'Penelope' (unpatented) and *Dahlia* 'Park Record' (unpatented). Whereas the predominant flower color of 'Peach Flamingo' is peach, the flowers of 'Penelope' and 'Park Record' are yellow with a pink edge, and dark orange respectively. Whereas the natural un-pinched height of 'Peach Flamingo' is 40 cm to 50 cm, plants of 'Penelope' and 'Park Record' are naturally taller at 70 cm and 60 cm respectively. Finally, whereas the stems of 'Peach Flamingo' are dark green in color, the stems of 'Penelope' and 'Park Record' are black in color.

I claim:

1. A new and distinct cultivar of *Dahlia* plant named 'Peach Flamingo' as described and illustrated herein.

* * * * *